United States Patent [19]
Swartz

[11] Patent Number: 4,735,605
[45] Date of Patent: Apr. 5, 1988

[54] LIPECTOMY DEVICE HAVING ROUND CUTTING EDGES

[76] Inventor: Barry E. Swartz, 13114 Huntersbrook, San Antonio, Tex. 78230

[21] Appl. No.: 907,505

[22] Filed: Sep. 15, 1986

[51] Int. Cl.$^4$ .............................................. A61B 17/20
[52] U.S. Cl. ..................... 604/22; 128/305; 128/755; 30/29.5; 604/902
[58] Field of Search ................. 433/110; 604/22, 264, 604/267, 902; 128/305, 311, 755; 74/89.15; 30/29.5, 263–265, 357

[56] References Cited

U.S. PATENT DOCUMENTS

| | | | |
|---|---|---|---|
| 2,919,911 | 1/1960 | Furtah, Jr. | 74/89.15 |
| 3,082,805 | 3/1963 | Royce | 128/755 |
| 3,732,858 | 5/1973 | Banko | 128/2 B |
| 3,734,099 | 5/1973 | Bender et al. | 128/305 |
| 3,955,579 | 5/1976 | Bridgman | 128/304 |
| 4,167,944 | 9/1979 | Banko | 17/32 |
| 4,203,444 | 5/1980 | Bonnell et al. | 128/276 |
| 4,311,140 | 1/1982 | Bridgman | 128/276 |

OTHER PUBLICATIONS

Body Contouring with Suction Lipectomy, by U. K. Kesselring, M.D., *Clinics in Plastic Surgery*, vol. 11, No. 3, Jul. 1984, pp. 393 through 417.

Primary Examiner—C. Fred Rosenbaum
Assistant Examiner—J. L. Kruter
Attorney, Agent, or Firm—Gunn, Lee & Jackson

[57] ABSTRACT

An improved lipectomy device, or cannula, is disclosed having inner and outer tubes. The outer tube has an elongated aspiration aperture, and the inner tube has a spiral slot. A mechanism inside the handle of the device causes the inner tube to rotate, creating a traveling hole effect along the aspiration aperture. This obviates the necessity of the surgeon repeatedly pushing the cannula in and out.

24 Claims, 2 Drawing Sheets

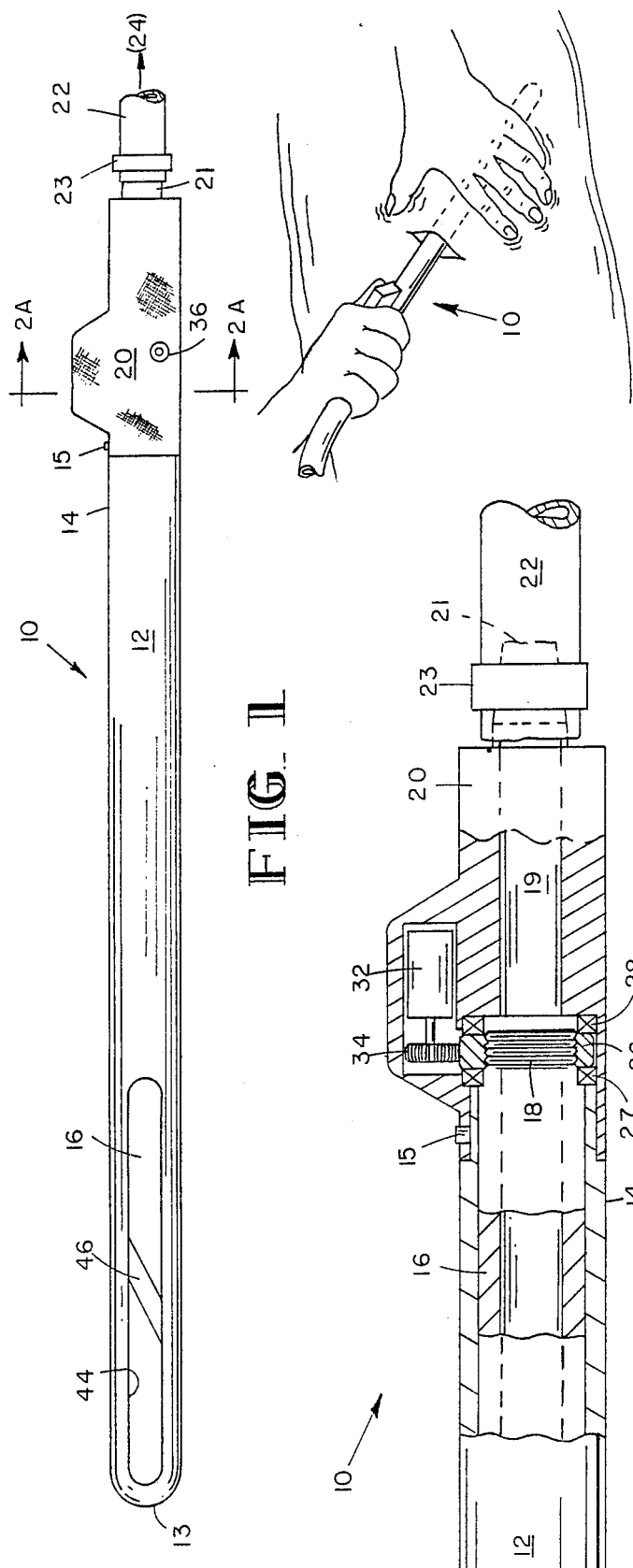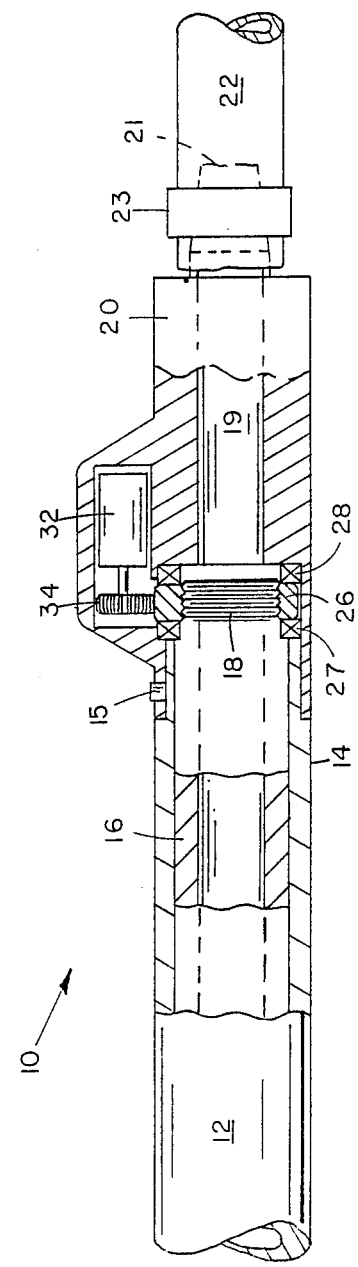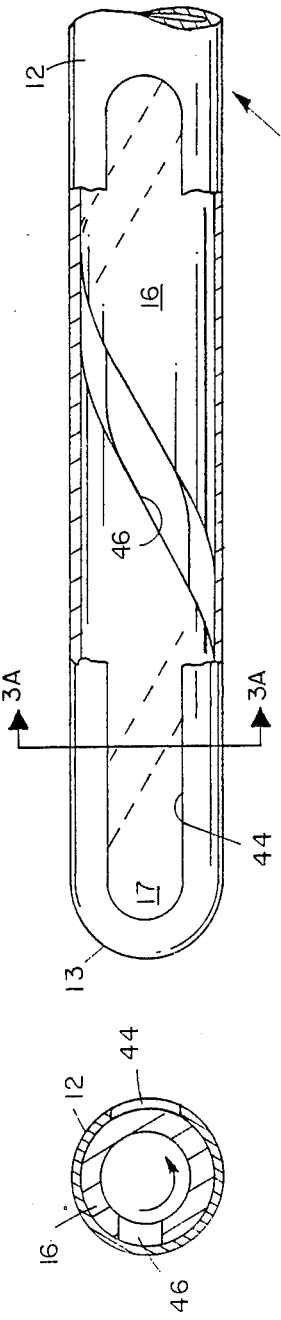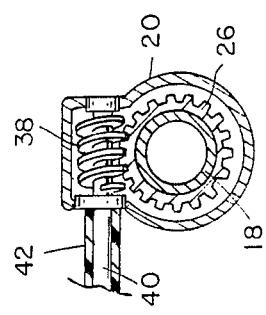

LIPECTOMY DEVICE HAVING ROUND CUTTING EDGES

BACKGROUND OF THE INVENTION

1. Field of the Invention

The present invention relates to a lipectomy device for removing unwanted fat, and more particularly to a motorized improvement of such a device.

2. Description of the Prior Art

Body sculpturing, or body contour surgery, is a routine procedure used to increase the attractiveness of the human form. One particular technique of body sculpturing involves suction lipectomy, also known as liposuction or lipexheresis (Greek for "fat suction").

This technique was first used in Europe by J. Schrudde in 1972, who used a uterine curet for this purpose. Such a curet is depicted in U.S. Pat. No. 3,955,579, issued to Bridgmann on May 11, 1976. An improved curet is shown in U.S. Pat. No. 4,311,140, also to Bridgman, on Jan. 19, 1982.

Although this technique was first treated with some apprehension, it has now become widely accepted by both the medical community and by the layman. It can be practiced by physicians with different backgrounds, e.g., general practitioners, dermatologists, otorhinolaryngologists, or gynecologists, although it is most often performed by plastic surgeons. It has been used to remove fat from all over the body. The regions most frequently treated include the trochanteric region, flanks, buttocks, inner aspect of the knee, the anterior abdominal wall, gynecomastia, and "lovehandles". Although it was once believed that the fat cells so removed would later be replaced, the present accepted theory is that the body contains a limited number of fat cells that cannot regenerate. Fatty tissue is thus caused not by an increase in the number of fat cells, but by an increase in the amount of lipid matter found within the cell boundaries. Therefore, it is thought that removal of the fat cells by liposuction will create a contour that will retain its form.

Today the procedure is performed using a special type of curet known as a cannula. One excellent article discussing various shapes and sizes of cannulas is "Body Contouring with Suction Lipectomy" by Kesselring, published in Clinics in Plastic Surgery, Vol. 11, No. 3 (July 1984). One cannula often used is known as the Aspiradeps, manufactured by Ulrich A. G., in St. Gall, Switzerland. The cannula is attached to a vacuum source which carries away the fat tissue. The vacuum pressure is usually on the order of 0.4 to 0.6 atmospheres.

There are two accepted techniques practiced today. The first is the tunneling procedure proposed by Illouz. In this method, one or two incisions are made, with radical excursions of the instrument into the flesh. The result is a multitude of concomitant sinuses. The second, the most common method, is the original liposuction procedure proposed by Kesselring. In that technique, an entire layer of regular, deep fat is removed, leaving a smooth, deep surface of the residual panniculus. The space thus created is then compressed, optionally followed by skin retraction.

Both of theses techniques require that the surgeon push and pull the entire cannula back and forth about twenty times for each incision made. Normally, twenty to thirty incisions, or tunnels, are made. This is necessary to insure even removal of fat in the targeted region. The surgeon typically massages the flesh in the area of the aperture in the cannula, while at the same time thrusting the rod in and out of the tunnel. This is an extremely traumatic method, both for the patient and the doctor. The patient's flesh turns black and blue for several days. Moreover, many surgeons practicing this technique find it physically exacting, and most come out of the operating room extremely tired. It would therefore be desirable and advantageous to device an improved cannula which would assist the surgeon in the lipectomy procedure, decreasing the amount of trauma to the tissues and decreasing the physical exertion expended by the surgeon.

SUMMARY OF THE INVENTION

Accordingly, the primary object of the present invention is to provide an improved lipectomy device which will assist the surgeon in the removal of fat from surrounding tissue.

Another object of the invention is to provide such a device which will reduce general trauma to the tissue of the patient.

Yet another object of the invention is to provide such a device which will reduce localized trauma to blood vessels, nerves, skin, muscles, and lymphatic tissue of the patient.

Still another object of the invention is to provide such a device that will allow minimal scarring, minimal pain and discomfort, minimal risks, and a faster recovery period.

The foregoing objects are achieved in an assisted lipectomy device having an outer tube with a longitudinal slot, and an inner rotating tube with a spiral slot, whereby a "traveling hole" is created which may more effectively remove fatty tissue.

BRIEF DESCRIPTION OF THE DRAWINGS

The novel features believed characteristic of the invention are set forth in the appended claims. The invention itself, however, as well as a preferred mode of use, further objects and advantages thereof, will best be understood by reference to the following detailed description of illustrative embodiments when read in conjunction with the accompanying drawings, wherein:

FIG. 1 is a side elevational view of the improved cannula of the present invention.

FIG. 2 is a partial cross-section of the cannula of the present invention showing the attachment of the inner and outer tubes to gear assembly and handle.

FIG. 2A is a cross-section of the cannula of the present invention taken along lines 2A—2A of FIG. 1 showing an alternative gear assembly.

FIG. 3 is partial cross-section of the cannula of the present invention showing the interaction of the spiral slot of the inner tube and the longitudinal slot of the outer tube.

FIG. 3A is a cross-section of the tip of the cannula taken along lines 3A—3A of FIG. 3.

FIG. 4 is a perspective of the improved cannula of the present invention depicting actual use of the device.

FIG. 5 is a front view of the drive gear and tube gear arrangement shown in FIG. 2.

DESCRIPTION OF THE PREFERRED EMBODIMENTS

Figure 3B:
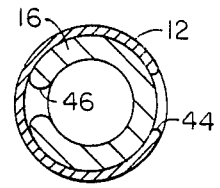
FIG. 3B is a cross-section of the cannula of the present invention showing the edges thereof.

With reference now to the figures, and in particular with reference to FIG. 1, there is depicted a side view of the improved cannula 10 of the present invention. Improved cannula 10 comprises an outer tube 12, an inner tube 16, a handle 20, and a hose 22 leading to a vacuum source 24 (not shown). Cannula 10 may be any length up to 45 cm., but it generally depends on the location of the fat deposits. A 30 cm. cannula is preferred for the larger areas such as the buttocks, hips, and "saddlebags." A 10 cm. cannula is preferred for the knees, ankles, abdomen, and arms, and a 5 cm. or smaller cannula is required for the face. The diameter of the cannula is likewise variable, generally within the range of five to twenty-five millimeters. The distal end 13 of outer tube 12 should be slightly rounded or bullet-shaped. If the end were pointed or sharp, it might puncture vital organs or blood vessels within the body. If the end were totally flat, it would cause excessive damage to the fatty tissues. Handle 20 is preferably made of a resilient material, such as metal or hard plastic. Integral with handle 20 is port 21. Hose 22 is attached to port 21 by means of clamp 23, and should be made of a clear plastic.

With further reference to FIG. 2, it can be seen that inner tube 16 rotates within fixed outer tube 12 by means of a tube gear 26. The proximate end 14 of outer tube 12 is attached to handle 20 by means of a conventional twist and lock arrangement 15. The proximate end 18 of inner tube 16 is threaded and engages with inner tube gear 26. Tube gear 26 is held in place by bearings 27 and 28.

One advantage of this attachment method is the interchangeability of different sizes of inner and outer tubes. Although most cannulas today are made of surgical steel, it is envisioned that the outer and inner tubes 12 and 16 may be made of hard plastic or other easily manufactured material so as to make them disposable. The surface of inner tube 16 may be coated with an anti-friction compound such as Teflon (polytetrafluoroethylene) to ease the rotation thereof within outer tube 12.

Two alternate means of driving tube gear 26 are contemplated. The first, depicted in FIGS. 2 and 5, includes an electric motor 32 housed within handle 20. Motor 32 would require a power cord (not shown) for connection to a source of electricity. Motor 32 powers drive gear 34 which in turn engages tube gear 26. Motor 32 may be activated by a thumb-operated on/off switch 36. Motor 32 may be air-driven instead of electric.

The second, and preferred, driving means is shown in FIG. 2A. This consists of a worm gear 38 engaged with tube gear 26. Worm gear 38 is powered by a rotating steel cable 40, located within a protective sheath 42. Cable 40 is powered by remote motor means, and controlled by a foot pedal (not shown). An example of such an arrangement is the cable system manufactured by Dermatomes for use with skin grafts. In this embodiment, element 36 may simply be a dimple for the thumb so that the operator is aware of the orientation of cannula 10.

With reference now to FIGS. 3 and 3A, it can be seen that both outer and inner tubes 12 and 16 are hollow. Outer tube 12 has a longitudinal slot 44 which generally corresponds to the aspiration apertures of the prior art cannulas. However, longitudinal slot 44 is much longer than those apertures. Although slot 44 may extend the entire length of outer tube 12, it is preferred, for reasons discussed below, that its length be approximately the width of a normal human hand, or about 8 cm., and begin near the distal end 13 of outer tube 12. It should be at least 4 cm. long. The width of slot 44 should be between three and twenty millimeters, and preferably about 5 mm.

Inner tube 16 has a spiral slot 46 located near its distal end 17 so as to coincide with longitudinal slot 44 of outer tube 12. The effective length of spiral slot 46 should correspond to the length of longitudinal slot 44. Spiral slot 46 may make several revolutions around inner tube 16, but it is preferred that spiral slot 46 make only one 360° rotation along this length. Thereby, when inner tube 16 rotates, a "traveling hole" appears in longitudinal slot 44. The width of spiral slot 46 may be between three and twenty millimeters, preferably 12 mm. This feature obviates the necessity of the surgeon repeatedly pushing the cannula 10 to and fro, facilitating the entire operation and minimizing discomfort to the patient.

The direction of rotation of inner tube 16 should complement the threading of proximate end 18, so as to keep inner tube 16 engaged with tube gear 26. If proximate end 18 has right-handed male threads, the direction of rotation of inner tube 16 is counterclockwise as shown in FIG. 3A.

In the preferred embodiment, the edges of longitudinal slot 44 and spiral slot 46 are rounded rather than sharp. The functional differences between a rounded edge and a sharp edge are only apparent in the way in which the fat lobules are removed from their nutrient vessels. With the rounded edge, the fat lobules are torn off (avulsion) by the suction power across the edge of the slot, with minimal damage to the nutrient vessels; with a sharp edge, they are cut off (section) while being sucked into the tube. With the latter device, there exists a chance that the nutrient vessels themselves, or nerves or lymphatic tissue, may be cut, which is obviously undesirable. The fat will then be conveyed down the center of inner tube 16, through cavity 19 in handle 20, and out port 21 and hose 22.

In an equivalent embodiment, the locations of the spiral and longitudinal slots could be reversed, placing the spiral slot on outer tube 12 and the longitudinal slot on inner tube 16. This approach, however, has certain drawbacks. First of all, the "traveling hole" would rotate around the cannula, making it impossible to concentrate on a given layer of fat. This would also result in excessive trauma to the surrounding tissue, and require a more powerful motor. Alternately, the inner tube may be similar to piston, and have an annular slot which would slide along the inside of the longitudinal slot.

OPERATION

Existing procedures for preparing the patient for the lipectomy may be used in operations employing the improved cannula 10. The regions to be suctioned should be demarcated depending on the technique to be used. Anesthesia can be general, peridural, or local. The patient should be in either the prone or supine position depending on the targeted area. A saline or distilled water solution may be infiltrated in the fatty deposits.

An incision is made in the skin from 5 to 20 mm. in length depending on the diameter of the cannula. The device 10 is then inserted into the incision, creating a tunnel at the deep level of the tissue, near the fascia. This is necessary to avoid the lymphatics contained in the subcutaneous fat, and to retain skin trophicity and tonicity. The vacuum source 24 is then activated. A negative pressure of 0.3 to 1.5 atm. is required, depending on the size of the slots 44 and 46. It is anticipated that the optimum negative pressure for a cannula having an longitudinal slot width of 6 mm. and a spiral slot width of 12 mm. would be 1.0 atm.

When the cannula 10 is in place and the vacuum is turned on, the operator should activate the rotation of inner tube 16 by using the foot pedal, in the case of the preferred worm gear mechanism 38, or by depression of switch 36 in the case of the motor 32 within handle 20. As depicted in FIG. 4, the operator should then begin to gently massage the region. The aspirated fat will be seen in hose 22. Fat is pure yellow, and if blood appears in the tubing the operator should change the orientation of cannula 10, or remove it. Filter units (not shown) may be attached to hose 22 before the vacuum source to keep track of the amount of fat and blood removed. After 100 cc. of fat have been removed, a new tunnel should be made and the procedure repeated. It is advisable to remove no more than six pounds of fatty tissue in order to avoid shock and other complications.

When the removal is complete, compression bandages should be applied. More than one operation may be necessary. Skin retraction may follow.

Although the invention has been described with reference to specific embodiments, this description is not meant to be construed in a limiting sense. Various modifications of the disclosed embodiments, as well as alternative embodiments of the invention will become apparent to persons skilled in the art upon reference to the description of the invention. It is therefore contemplated that the appended claims will cover such modifications that fall within the true scope of the invention.

I claim:
1. An assisted lipectomy device, comprising:
   handle means;
   an outer tube having distal end proximate ends, and having a first longitudinal slot, said outer tube being open at said proximate end, and said proximate end of said outer tube attached to said handle means;
   an inner tube having distal and proximate ends, and having a second spiral slot, said inner tube located within said outer tube, said inner tube being open at said proximate end, and said proximate end of said inner tube attached to said handle means;
   vacuum means in fluid communication with said inner tube for creating suction within said inner tube;
   said spiral and longitudinal slots each having rounded cutting edges;
   motor means coupled to said inner tube for rotating said inner tube along their length to remove fat lobules by tearing in conjunction with said vacuum means.

2. An assisted lipectomy device as recited in claim 1 further comprising:
   first and second ends of said handle means, said handle means having a cavity extending from said first end to said second end, said proximate end of said outer tube and said proximate end of said inner tube being attached to said first end of said handle means;
   a port attached to and integral with said second end of said handle means; and
   a hose attached to said port, said hose connecting said handle means to said vacuum means.

3. An assisted lipectomy device as recited in claim 2 wherein said vacuum means comprises a vacuum pump capable of delivering a negative pressure between 0.3 to 1.5 atmospheres.

4. An assisted lipectomy device as recited in claim 2 wherein said proximate end of said outer tube is attached to said first end of said handle means by a twist and lock arrangement.

5. An assisted lipectomy device as recited in claim 3 further comprising:
   a tube gear located within said handle means;
   said tube gear having an aperture therein, forming an inner surface, said inner surface being threaded;
   said proximate end of said inner tube being threaded for engagement with said inner surface of said tube gear;
   bearing means for containing said tube gear within said handle means; and
   said motor means coupled to said tube gear.

6. An assisted lipectomy device as recited in claim 5 wherein said motor means is comprised of:
   an electric motor located within said handle means;
   a power cord for connection of said motor to a source of electricity; and
   a drive gear coupled to said motor, said drive gear engaging said tube gear.

7. An assisted lipectomy device as recited in claim 5 wherein said motor means is comprised of:
   an air-driven motor located within said handle means;
   an air pump remote from but fluidly connected to said motor;
   a drive gear coupled to said motor, said drive gear engaging said tube gear.

8. An assisted lipectomy device as recited in claim 5 wherein said motor means is comprised of:
   a motor remote from said handle means;
   a flexible steel cable having a first end and a second end, said first end rotatably connected to said motor;
   a worm gear located within said handle means, attached to said second end of said cable, and engaging said tube gear.

9. An assisted lipectomy device as recited in claim 1 further comprising:
   a tube gear located within said handle means;
   said tube gear having an aperture therein, forming an inner surface said inner surface being threaded;
   said proximate end of said inner tube being threaded for engagement with said inner surface of said tube gear;
   bearing means for containing said tube gear within said handle means; and
   said motor means coupled to said tube gear.

10. An assisted lipectomy device as recited in claim 9 wherein said motor means is comprised of:
    an electric motor located within said handle means;
    a power cord for connection of said motor to a source of electricity; and
    a drive gear coupled to said motor, said drive gear engaging said tube gear.

11. An assisted lipectomy device as recited in claim 9 wherein said motor means is comprised of:
    an air-driven motor located within said handle means;

an air pump remote from but fluidly connected to said motor;

a drive gear coupled to said motor, said drive gear engaging said tube gear.

12. An assisted lipectomy device as recited in claim 9 wherein said motor means is comprised of:

a motor remote from said handle means;

a flexible steel cable having a first end and a second end, said first end rotatably connected to said motor;

a worm gear located within said handle means, attached to said second end of said cable, and engaging said tube gear.

13. An assisted lipectomy device as recited in claim 1 wherein said inner and outer tubes have a length between 4 and 45 centimeters.

14. An assisted lipectomy device as recited in claim 1 wherein said inner and outer tubes have a diameter between 5 and 25 millimeters.

15. An assisted lipectomy device as recited in claim 1 wherein said longitudinal slot has a length of at least 4 centimeters.

16. An assisted lipectomy device as recited in claim 1 wherein said longitudinal slot has a width between 3 and 20 millimeters.

17. An assisted lipectomy device as recited in claim 1 wherein said spiral slot has an effective length approximately equal to the length of said longitudinal slot.

18. An assisted lipectomy device as recited in claim 1 wherein said spiral slot has a width between 3 and 20 millimeters.

19. An assisted lipectomy device comprising:

a handle having first and second ends, and having a cavity extending from said first end to said second end;

a tube gear located inside said cavity, said tube gear having an aperture therein, forming an inner surface, said inner surface being threaded;

bearing means for containing said tube gear within said cavity;

motor means coupled to said tube gear;

switch means for activating said motor means;

an inner tube having distal and proximate ends, said proximate end of said inner tube passing through said first end of said handle, being open and threaded for mating with said threaded inner surface of said tube gear, and said inner tube having a spiral slot located near said distal end;

an outer tube having distal and proximate ends and surrounding said inner tube, said proximate end of said outer tube being attached to said first end of said handle by a twist and lock arrangement, said outer tube having a longitudinal slot located near said distal end;

a vacuum means in fluid communication with said inner tube for creating suction within said inner tube;

said spiral and longitudinal slots each having rounded cutting edges along their length to remove fat lobules by tearing in conjunction with said vacuum means;

a port attached to an integral with said second end of said handle;

a hose attached to said port connecting said handle to said vacuum means.

20. An assisted lipectomy device as recited in claim 19 wherein said motor means is comprised of:

an electric motor located within said handle means;

a power cord for connection of said motor to a source of electricity; and a drive gear coupled to said motor, said drive gear engaging said tube gear.

21. An assisted lipectomy device as recited in claim 19 wherein said motor means is comprised of:

an air-driven motor located within said handle means;

an air pump remote from but fluidly connected to said motor;

a drive gear coupled to said motor, said drive gear engaging said tube gear.

22. An assisted lipectomy device as recited in claim 19 wherein said motor means is comprised of:

a motor remote from said handle means;

a flexible steel cable having a first end and a second end, said first end rotatably connected to said motor;

a worm gear located within said handle means, attached to said second end of said cable, and engaging said tube gear.

23. An assisted lipectomy device as recited in claim 19 wherein said inner and outer tubes have a length between 4 and 45 centimeters, and a diameter between 5 and 25 millimeters.

24. An assisted lipectomy device as recited in claim 19 wherein:

said longitudinal slot has a length of at least 4 centimeters, and a width between 3 and 20 millimeters; and said spiral slot has an effective length approximately equal to said length of said longitudinal slot, and a width between 3 and 20 millimeters.

* * * * *